(12) United States Patent
Maher et al.

(10) Patent No.: US 8,466,195 B2
(45) Date of Patent: Jun. 18, 2013

(54) METHODS AND COMPOSITIONS FOR TREATING COMPLICATIONS OF DIABETES AND VASCULAR DISEASES USING FLAVONES

(75) Inventors: Pamela A. Maher, La Jolla, CA (US); David R. Schubert, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 81 days.

(21) Appl. No.: 13/255,192

(22) PCT Filed: Mar. 15, 2010

(86) PCT No.: PCT/US2010/027287
§ 371 (c)(1),
(2), (4) Date: Oct. 3, 2011

(87) PCT Pub. No.: WO2010/105253
PCT Pub. Date: Sep. 16, 2010

(65) Prior Publication Data
US 2012/0016016 A1   Jan. 19, 2012

Related U.S. Application Data

(60) Provisional application No. 61/160,171, filed on Mar. 13, 2009.

(51) Int. Cl.
*A61K 31/353* (2006.01)
(52) U.S. Cl.
USPC ........................................................ 514/456
(58) Field of Classification Search
USPC ........................................................ 514/456
See application file for complete search history.

(56) References Cited

U.S. PATENT DOCUMENTS 4,428,876 A   1/1984 Iwamura
5,702,752 A   12/1997 Gugger et al.

OTHER PUBLICATIONS

Anjaneyulu, M. et al., "Quercetin attenuates thermal hyperalgesia and cold allodynia in STZ-induced diabetic rats", Indian Journal of Experimental Biology, Aug. 2004, 42:766-769.
Anjaneyulu, M. et al., "Quercetin, an anti-oxidant bioflavonoid, attenuates diabetic nephropathy in rats", Clinical and Experimental Pharmacology and Physiology, 2004, 31:244-248.
Arai, Y. et al., "Dietary intakes of flavonols, flavones and isoflavones by Japanese women and the inverse correlation between quercetin intake and plasma LDL cholesterol concentration", J. Nutr., 2000, 130:2243-2250.
Berge, S.M. et al., "Pharmaceutical Salts", Journal of Pharmaceutical Science, Jan. 1977, 66(1):1-19.
Calcutt, N.A. et al., "Coexistence of nerve conduction deficit with increased $Na^+$—$K^+$—ATPase activity in galactose-fed mice", Diabetes, Jun. 1990, 39:663-666.
Calcutt, N.A. et al., "Therapies for hyperglycaemia-induced diabetic complications: from animal models to clinical trials", Nature Review, May 2009, 8:417-429.
Geraets, L. et al., "Inhibition of LPS-induced pulmonary inflammation by specific flavonoids", 2009, Biochemical Biophysical Research Communications 382:598-603.
Hatcher, H. et al., "Curcumin: from ancient medicine to current clinical trials", Cell and Molecular Life Sciences, 2008, 65:1631-1652.
International Preliminary Report on Patentability and Written Opinion dated Sep. 13, 2011 for International PCT Application No. PCT/US2010/027287, 5 pages.
Ishige, K. et al., "Flavonoids protect neuronal cells from oxidative stress by three distinct mechanisms", Free Radical Biology & Medicine, 2001, 30:433-446.
Ji, H.F. et al., "Natural products and drug discovery", EMBO Reports, 2009, 10:194-200.
King, G.L., "The role of inflammatory cytokines in diabetes and its complications", J. Periodontol, Aug. 2008, 79:1527-1534.
Li, Y. et al., "A role of 12-lipoxygenase in nerve cell death caused by glutathione depletion", Neuron, Aug. 1997, 19:453-463.
Maher, P., "Modulation of multiple pathways involved in the maintenance of neuronal function by fisetin", 2010, In: Packer L, Sies H, Eggersdorfer M, Cadenas E (eds) Micronutrients and Brain Health. CRC Press, Boca Raton, FL, pp. 189-206.
Maher, P. et al., "Modulation of multiple pathways involved in the maintenance of neuronal function during aging by fisetin", 2009, Genes Nutr 4:297-307.
Maher, P. et al., "Flavonoid fisetin promotes ERK-dependent long-term potentiation and enhances memory", Proc Natl Acad Sci USA, Oct. 31, 2006, 103:16568-16573.
Prasain, J.K. et al., "Metabolism and bioavailability of flavonoids in chemoprevention: Current analytical strategies and future prospectus", Molecular Pharmaceutics, 2007, 4:846-864.
Sagara, Y. et al., "Induction of PC12 cell differentiation by flavonoids is dependent upon extracellular signal-regulated kinase activation", Journal of Neurochemistry, 2004, 90:1144-1155.
Sando, C.E. et al., "The flavones of rhus", American Journal of Botany, Mar. 1918, 5(3):112-119.
Sharma, S. et al., "Resveratrol, a polyphenolic phytoalexin, attenuates diabetic nephropathy in rats", 2006, Pharmacology 76:69-75.
Sharma, S. et al., "Curcumin attenuates thermal hyperalgesia in a diabetic mouse model of neuropathic pain", European Journal of Pharmacology, 2006, 536:256-261.
Sharma, S. et al., "Curcumin, the active principle of tumeric (*Curcuma longa*), ameliorates diabetic nephropathy in rats", Clinical and Experimental Pharmacology and Physiology, 2006, 33:940-945.
Sharma, S. et al., "Effect of resveratrol, polyphenolic phytoalexin, on thermal hyperalgesia in a mouse model of diabetic neuropathic pain", Fundamental & Clinical Pharmacology, 2007, 21:89-94.
Shia, C-S et al., "Metabolism and pharmacokinetics of 3,3',4',7-tetrahydroxyflavone (fisetin), 5-hydroxyflavone and (Continued)

*Primary Examiner* — Raymond Henley, III
(74) *Attorney, Agent, or Firm* — Kilpatrick Townsend & Stockton LLP

(57) ABSTRACT

Disclosed herein, inter alia, are methods and compositions for treating a complication of diabetes or a vascular disease using a 5-desoxy-flavone and/or 5-desoxy-flavonol.

15 Claims, 10 Drawing Sheets

OTHER PUBLICATIONS 7-hydroxyflavone and antihemolysis effects of fisetin and its serum metabolites", Journal of Agricultural and Food Chemistry, 2009, 57:83-89.

Son, Y-O et al., "Selective antiproliferative and apoptotic effects of flavonoids purified from *Rhus verniciflua* stokes on normal versus transformed hepatic cell lines", Toxicology Letters, 2005, 155:115-125.

Stirban, A. et al., "Complications of Type 1 diabetes: new molecular findings", Mount Sinai Journal of Medicine, 2008, 75:328-351.

Valensi, P. et al., "A mulitcenter, double-blind, safety study of QR-333 for the treatment of symptomatic diabetic peripheral neuropathy a preliminary report", Journal of Diabetes and Its Complications, 2005, 19:247-253.

Wang, L. et al., "Distinctive antioxidant and antiinflammatory effects of flavonols", Journal of Agricultural and Food Chemistry, 2006, 54:9798-9804.

Zheng, L.T. et al., "Suppressive effects of flavonoid fisetin on lipopolysaccharide-induced microglial activation and neurotoxicity", International Immunopharmacology, 2008, 8:484-494.

Fisetin Reduces the Impact of Diabetes on Nerve Function

A

B

Figure 3 of manuscript and Figure 6 of provisional

Fisetin Reduces the Impact of Diabetes on Kidney Function

(Figure 1 of manuscript and Figure 7 of provisional

Fisetin Increases Locomotor Activity and Decreases Immobilization in Diabetic Mice

Figure 4 in Mansucript

METHODS AND COMPOSITIONS FOR TREATING COMPLICATIONS OF DIABETES AND VASCULAR DISEASES USING FLAVONES

CROSS-REFERENCES TO RELATED APPLICATIONS

This application claims the benefit of U.S. Provisional Application No. 61/160,171, filed Mar. 13, 2009, the contents of which are herein incorporated by reference for all purposes.

STATEMENT AS TO RIGHTS TO INVENTIONS MADE UNDER FEDERALLY SPONSORED RESEARCH AND DEVELOPMENT

This invention was made with United States government support under grant number DK063491 awarded by the National Institutes of Health. The United States government has certain rights in the invention.

BACKGROUND OF THE INVENTION

The complications of diabetes are the major cause of both morbidity and mortality in patients with the disease [for reviews see 1, 2]. These complications arise from diabetes-specific effects on the microvasculature in the retina, kidney and peripheral and central nervous systems and diabetes-accelerated effects on the macrovasculature leading to atherosclerosis and its ensuing consequences. Diabetes-specific effects on other cell types including nerve cells, glomerular cells, adipocytes and vascular smooth muscle cells also contribute to the development of diabetic complications. The chronic hyperglycemia associated with diabetes is thought to be the major cause of these complications. The consequences of hyperglycemia are complex and appear to alter multiple (patho)-physiological processes including oxidative stress, protein glycation, mitochondrial function and inflammation. Glucose-independent processes may also contribute to specific diabetic complications [2]. Therefore, it is unlikely that hitting a single target will result in significant benefits to patients with diabetes. However, current drug research efforts are almost exclusively focused on single protein targets and the identification of small molecules that can modulate these targets with high affinity. Disclosed herein are methods and compositions to address these and other problems in the art.

BRIEF SUMMARY OF THE INVENTION

In one aspect, a method is provided for treating a complication of a diabetes or a vascular disease in a subject in need thereof. The method includes administering to the subject a therapeutically effective amount of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below.

In another aspect, a method of treating a nephropathy and a neuropathy in a subject in need thereof having a vascular disease or diabetes is provided. The method includes administering to the subject a therapeutically effective amount of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below.

In another aspect, a method of decreasing C-reactive protein levels in a subject in need thereof is provided. The method includes administering to the subject an effective amount (e.g. a therapeutically effective amount for treating an inflammation) of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below.

DEFINITIONS

The term "Diabetes" as used herein, is also commonly referred to as Diabetes mellitus, includes all known types of Diabetes, including Type 1 diabetes, Type 2 diabetes, Gestational diabetes, etc.

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Acyl" refers to a group having the structure —C(O)R, where R may be alkyl or substituted alkyl. "Lower acyl" groups are those that contain from 1 to 10 (such as from 1 to 6) carbon atoms.

"Acyloxy" refers to a group having the structure —OC(O)R, where R may be optionally substituted alkyl or optionally substituted aryl. "Lower acyloxy" groups are those where R contains from 1 to 10 (such as from 1 to 6) carbon atoms.

"Alkoxy" refers to a group having the formula —OR, wherein R is an alkyl group "Lower alkoxy" refers to an —OR group in which the R group has from 1 to 10 carbon atoms, such as from 1 to 6 carbon atoms. Examples of lower alkoxy groups include, but are not limited to, methoxy, ethoxy, n-propoxy, isopropoxy and butoxy groups.

"Alkoxy carbonyl" refers to a group of the formula —C(O)OR, where R may be optionally substituted alkyl or optionally substituted aryl. "Lower alkoxy carbonyl" groups are those where R contains from 1 to 10 (such as from 1 to 6) carbon atoms.

A flavone is compound having the Base Structure:

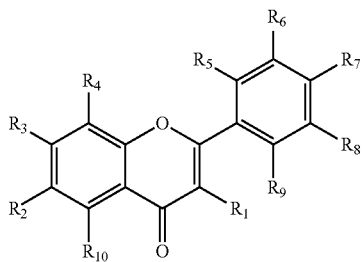

where any one or more of the $R_1$, $R_2$, $R_3$, $R_4$, $R_5$, $R_6$, $R_7$, $R_8$, $R_9$, or $R_{10}$ independently are hydrogen, alkyl (such as lower alkyl, e.g., methyl or ethyl), hydroxyl, or a substituent that may be metabolized in vivo to a hydroxyl group (e.g., acyl, acyloxy, and/or alkoxy). A flavone where $R_{10}$ is not a hydroxyl group is referred to as a "5-desoxy-flavone." A flavone where $R_{10}$ is hydrogen is referred to as a "5(H)-flavone."

A 3-hydroxy flavone (where $R_1$ is hydroxyl) is more particularly referred to as a "flavonol." Accordingly, a flavonol has the base structure:

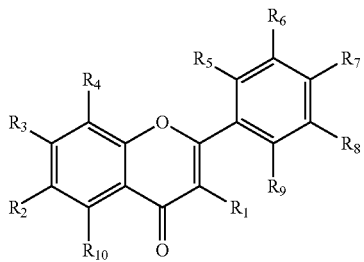

where $R_1$, $R_2$, $R_5$, $R_6$, $R_7$, $R_8$, $R_9$, or $R_{10}$ are as described for a flavone. A flavonol where $R_{10}$ is not a hydroxyl group is referred to as a "5-desoxy-flavonol." A flavonol where $R_{10}$ is hydrogen is referred to as a "5(H)-flavonol."

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

The phrase "effective amount" refers to an amount sufficient to attain the desired result. The phrase "therapeutically effective amount" means an amount sufficient to produce the desired therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

The terms "treat," "treating" or "treatment," and other grammatical equivalents as used herein, include alleviating, abating or ameliorating a disease or condition symptoms (such as diabetic complication or vascular disease complication), preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made

DETAILED DESCRIPTION

I. Methods

Figure 1:
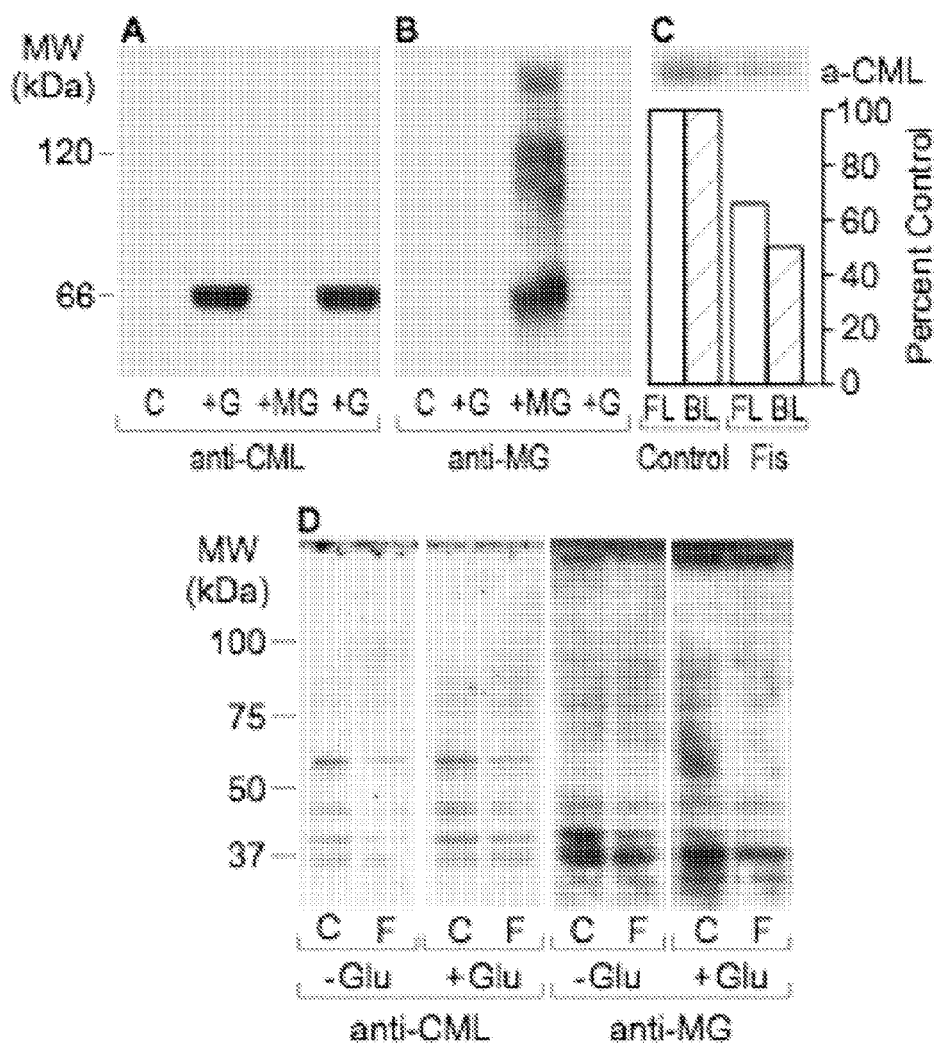
FIG. 1 illustrates the specificity of antisera and inhibition of glycation by fisetin.

In one aspect, a method is provided for treating a complication of a diabetes or a vascular disease in a subject in need thereof. The method includes administering to the subject a therapeutically effective amount of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below. In some embodiments, the subject has diabetes (e.g. Type I diabetes or Type II diabetes). In some embodiments, the diabetes is Type I diabetes. In other embodiments, the diabetes is Type II diabetes.

A "complication" of diabetes or vascular disease, as used herein, refers to a disease or disorder that occurs during the course of (e.g. because of) a diabetes or a vascular disease. Complications of diabetes and vascular diseases are well known in the art, and include, for example, nephropathy (e.g. progressive loss of kidney function), neuropathy (e.g. respiratory autonomic neuropathy and structural derangement of the thorax and lung parenchyma), anxiety, inflammation, retinopathy, high blood pressure, blood vessel changes, muscle infarction, idiopathic skeletal hyperostosis and bone loss, foot ulcers, arteriosclerosis, left ventricular hypertrophy, cardiovascular morbidity, and anemia.

In some embodiments, the complication is a nephropathy. The nephropathy may be a diabetic nephropathy. In other embodiments the complication is a neuropathy. The neuropathy may be a diabetic neuropathy. In certain embodiments, the complication is a retinopathy, such as diabetic retinopathy. And in other embodiments, the complication is anxiety.

In certain embodiments, the administration of 5-desoxy-flavone and/or 5-desoxy-flavonol is effective in treating more than one complication simultaneously. For example, in some embodiments, the method treats a nephropathy and a neuropathy by administering an effective amount of 5-desoxy-flavone and/or 5-desoxy-flavonol. In some embodiments, in addition to a nephropathy and a neuropathy, the method further treats inflammation and/or anxiety in the subject.

Therefore, in another aspect, a method of treating a nephropathy and a neuropathy in a subject in need thereof having a vascular disease or diabetes is provided. The method includes administering to the subject a therapeutically effective amount of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below. In some embodiments, the subject has diabetes (e.g. Type I diabetes or Type II diabetes). In some embodiments, the diabetes is Type I diabetes. In other embodiments, the diabetes is Type II diabetes.

In certain embodiments, the nephropathy is a diabetic nephropathy and the neuropathy is a diabetic neuropathy. The diabetic neuropathy may be a diabetic retinopathy.

In some embodiments, the method is a further method of treating anxiety in the subject, wherein the subject is in need thereof. In other embodiments, the method is further a method of treating inflammation in the subject, wherein the subject is in need thereof.

In another aspect, a method of decreasing C-reactive protein levels in a subject in need thereof is provided. The method includes administering to the subject an effective amount (e.g. a therapeutically effective amount for treating an inflammation) of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below. In some embodiments, the subject has diabetes or a vascular disease. In some embodiments, the subject has diabetes (e.g. Type I diabetes or Type II diabetes). In some embodiments the subject has Type I diabetes. In other embodiments, the diabetes the subject has Type II diabetes. The C-reactive protein levels in the subject is decreased relative to the level of C-reactive protein in the subject in the absence of the 5-desoxy-flavone and/or 5-desoxy-flavonol. The C-reactive protein levels are typically measured from a serum sample obtained or derived from the subject using techniques known in the art.

In a another aspect, a methods of inhibiting (e.g. decreasing) AGE formation and/or for preventing or treating chronic tissue damage in a subject in need thereof is provided. The method includes administering to the subject an effective amount (e.g. a therapeutically effective amount for treating an inflammation) of a 5-desoxy-flavone and/or 5-desoxy-flavonol provided herein or a pharmaceutically acceptable salt thereof. In some embodiments, the 5-desoxy-flavone and/or 5-desoxy-flavonol forms part of a pharmaceutical composition as described below. In some embodiments, the subject has diabetes or a vascular disease. In some embodiments, the subject has diabetes (e.g. Type I diabetes or Type II diabetes). In some embodiments the subject has Type I diabetes. In other embodiments, the diabetes the subject has Type II diabetes.

In some subjects, administration of a 5-desoxy flavone or 5-desoxy flavonol (e.g., a 5(H)-flavone, a 5(H)-flavonol, such as fisetin or any one or more of its derivatives as described herein) may cause a detectable improvement in the subject as compared to an untreated subject (or the treated subject prior to treatment). For example, administration of the 5-desoxy flavone or 5-desoxy flavonol subject may diminish, prevent or reverse diabetic or vascular disease complications by at least about 10%, at least about 25%, at least about 50%, or at least about 75% as compared to a control (e.g., an untreated subject or the same subject prior to treatment).

Routes of administration useful in the disclosed methods include but are not limited to oral and parenteral routes, such as intravenous (iv), intraperitoneal (ip), subcutaneous (sc), intramuscular (im), rectal, topical, ophthalmic, nasal, or transdermal or topical (including buccal and sublingual). Formulations for these dosage forms are described in more detail below.

Therapeutically effective doses of a described flavonoid (e.g., 5-desoxy flavone or 5-desoxy flavonol (such as, fisetin or its derivatives) or pharmaceutical composition including the same can be determined by one of skill in the art. In some instances, an effective dose achieves a local (e.g., tissue) concentration that is at least as high as the EC 50 for neural protection or neural differentiation of the applicable compound disclosed in the examples herein; for example, from about 0.25 µM to about 200 µM, from about 0.5 µM to about 150 M, from about 0.75 µM to about 100 µM, from about 1 µM to about 75 µM, from about 1.5 µM to about 50 µM, from about 2.0 µM to about 40 µM, or from about 2.5 µM to about 20 µM (also, see Table 3 and/or 4).

A "subject" as used herein, refers to an animal subject. In some embodiments, the subject is a mammal, such as a domesticated animal or human.

Nephropathy typically refers to damage to, or a disease of, the kidney. Diabetic nephropathy refers to a kidney disease or kidney damage that is a complication of diabetes (e.g. Type 1 diabetes or Type 2 diabetes). Symptoms typically develop late in the disease and may include, for example, fatigue, a foamy appearance or excessive frothing of the urine, frequent hiccups, general ill feeling, generalized itching, headache, nausea and vomiting, poor appetite, swelling of the legs, swelling (e.g. around the eyes in the mornings or general body swelling), and unintentional weight gain (e.g. fluid buildup). Kidneys are composed of hundreds of thousands of filtering units called nephrons. Each nephron has a cluster of small blood vessels called a glomerulus. Together these structures help remove waste from the body. High blood sugar can damage these structures, causing them to thicken and become scarred.

As more and more blood vessels are destroyed, the kidney structures begin to leak and protein (albumin) begins to pass into the urine. Thus, a marker of diabetic nephropathy is persistent protein in the urine, which may be tested using a microalbuminuria test. Other markers may include serum creatinine, as well as blood levels of phosphorus, calcium, bicarbonate, PTH, and potassium.

Diabetic neuropathy is a common complication of diabetes, in which nerves are damaged as a result of high blood sugar levels (hyperglycemia). Symptoms may include, for example, constipation, diarrhea, nausea and vomiting, swallowing difficult, deep pain (e.g. in the feet and legs), loss of the sense of warm or cold, muscle cramps, numbness (e.g. if the nerves are severely damaged, a blister or minor wound may become infected), tingling or burning sensation in the extremities (e.g. the feet), weakness, dizziness, drooping eyelid, drooping face, drooping mouth, impotence, light-headedness when standing up (orthostatic hypotension), loss of bladder control, rapid heart rate, speech impairment, and vision changes.

Subjects with diabetes commonly develop temporary or permanent damage to nerve tissue. Nerve injuries may be caused by decreased blood flow and high blood sugar levels. On average, symptoms of nerve damage begin 10 to 20 years after the diabetes diagnosis. Approximately 50% of people with diabetes will eventually develop nerve damage. Peripheral nerve injuries may affect nerves in the skull (cranial nerves) or nerves from the spinal column and their branches. Neuropathy may develop in stages. Autonomic neuropathies affect the nerves that regulate vital functions, including the heart muscle and smooth muscles.

Neuropathy may be diagnosed using any appropriate method known in the art, such as a physical examination and/or nervous system (neurological) (e.g. sensory tests). Electrodiagnostic testing may also be performed.

Vascular diseases include conditions that affect the circulatory system, such as peripheral artery disease, and includes diseases of arteries, veins and lymph vessels as well as blood disorders that affect circulation. Thus, "vascular disease," as used herein, includes for example atherosclerosis, peripheral artery disease, aneurysms, renal artery disease, generalized vascular disease, Raynaud's Phenomenon, Buerger's Disease, superficial vein inflammation, peripheral venous disease, varicose veins, venous blood clots, congestive heart failure (CHF), deep vein thrombosis (DVT), pulmonary embolism, chronic venous insufficiency (CVI), blood clotting disorders, and lymphedema.

The present disclosure also contemplates combinations of one or more disclosed flavonoids (e.g., 5-desoxy flavone or 5-desoxy flavonol (such as, fisetin or its derivatives) with each other and/or with one or more other agents or therapies useful to improve and/or treat or prevent diabetes and diabetic complications disease. For example, one or more invention flavonoids described for use in a disclosed method may be administered in combination with effective doses of other medicinal and/or pharmaceutical agents (such as, nutraceuticals, vitamins, antioxidants, prescription medications, trace minerals, and the like), or in combination other therapies, such as hypnosis, acupuncture, or other so-called alternative medicines. The term "administration in combination with" refers to both concurrent and sequential administration of active agents. In some examples, the one or more other agents or therapies include vinpocetine (Cavinton™), piracetam (Nootropil™), or antioxidants (such as, Vitamin C, Vitamin E, alpha-carotene, beta-carotene, Coenzyme Q, selenium, zinc, manganese, lycopene, lutein, zeaxanthin, astaxanthin, or as otherwise known in the art).

II. 5-Desoxy-Flavone and/or 5-Desoxy-Flavonol Compounds 5-desoxy-flavones and/or 5-desoxy-flavonols useful in the disclosed methods may have the formula:

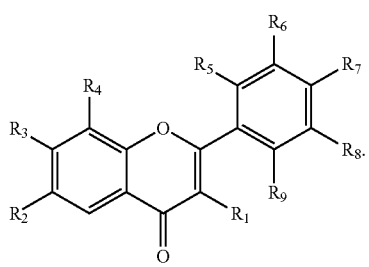

(I)

In Formula I, $R_1$, $R_2$, $R_3$, $R_4$, $R_5$, $R_6$, $R_7$, $R_8$, and $R_9$ are independently hydrogen, alkyl, hydroxyl, acyl, or alkoxy. In some embodiments, at least one of $R_6$ and $R_7$ is hydroxyl or acyl. And in certain embodiments, at least two of $R_1$, $R_3$, $R_6$, and $R_7$ are hydroxyl or acyl.

$R_1$, $R_2$, $R_3$, $R_4$, $R_5$, $R_6$, $R_7$, $R_8$, and $R_9$ may also independently be hydrogen, alkyl (such as lower alkyl, e.g., methyl or ethyl), hydroxyl, or a substituent that may be substantially cleaved in vivo to yield a hydroxy group (for example, by hydrolysis and/or by the action of one or more endogenous esterases). In some embodiments, at least one of $R_6$ and $R_7$ is hydroxyl or a substituent that may be substantially cleaved in vivo to a yield a hydroxy group. In certain embodiments, at least two of $R_1$, $R_3$, $R_6$, and $R_7$ are hydroxyl or a substituent that may be substantially cleaved in vivo to a hydroxy group. Examples of suitable groups for R 1-9 that can be cleaved in vivo to provide a hydroxy group include, without limitation, acyl, acyloxy and alkoxy carbonyl groups. Compounds having such cleavable groups are referred to as "prodrugs." The term "prodrug," as used herein, means a compound of Formula I which includes a substituent that is convertible in vivo (e.g. by hydrolysis) to a hydroxyl group. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). Design and Application of Prodrugs, Textbook of Drug Design and Development, Chapter 5, 113 191 (1991), Bundgaard, et al., Journal of Drug Deliver Reviews, 8:1 38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

In certain embodiments, $R_1$, $R_2$, $R_3$, $R_4$, $R_5$, $R_6$, $R_7$, $R_8$, and $R_9$ are independently hydrogen, alkyl (such as lower alkyl, e.g., methyl or ethyl), hydroxyl, for example acyloxy (such as lower acyloxy, for example acetyl or benzoyl), or alkoxy (such as lower alkoxy, e.g., methoxy); at least one of $R_6$ and $R_7$ is hydroxyl, acyl (such as lower acyl), or acyloxy (such as lower acyloxy); and at least two of $R_1$, $R_3$, $R_6$, and $R_7$ are hydroxyl, acyl (such as lower acyl), or acyloxy (such as lower acyloxy).

Other method embodiments involve compounds of Formula I, wherein $R_1$, $R_2$, $R_3$, $R_4$, $R_5$, $R_6$, $R_7$, $R_8$, and $R_9$ are independently hydrogen, hydroxyl, or acyl (such as lower acyl); at least one of $R_6$ and $R_7$ is hydroxyl or acyl (such as lower acyl); and at least two of $R_1$, $R_3$, $R_6$, and $R_7$ are hydroxyl or acyl (such as lower acyl). In some such embodiments, the substituent(s) indicated in Table I is (are each) hydroxyl and all other substituents are as described in this paragraph.

In particular examples, $R_1$, $R_2$, $R_3$, $R_4$, $R_5$, $R_6$, $R_7$, $R_8$, and $R_9$ are independently hydrogen, hydroxyl, or acyl (such as lower acyl); at least one of $R_6$ and $R_7$ is hydroxyl; and at least two of $R_1$, $R_3$, $R_6$, and $R_7$ are hydroxyl. In some such examples the substituent(s) indicated in Table I is (are each) hydroxyl and all other substituents are as described in this paragraph.

The 5-desoxy-flavone and/or 5-desoxy-flavonol may also include compounds represented by Formula II:

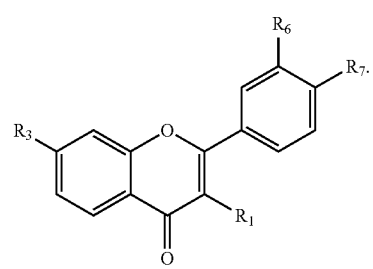

(II)

In Formula II, $R_1$, $R_3$, $R_6$, and $R_7$ may independently be hydrogen, alkyl (such as lower alkyl, e.g., methyl or ethyl), hydroxyl, or a substituent that may be substantially metabolized in vivo to a hydroxyl group; at least one of $R_6$ and $R_7$ is hydroxyl or a substituent that may be substantially metabolized in vivo to a hydroxyl group; and at least two of $R_1$, $R_3$, $R_6$, and $R_7$ are hydroxyl or a substituent that may be substantially metabolized in vivo to a hydroxyl group.

In some examples, $R_1$, $R_3$, $R_6$, and $R_7$ are independently hydrogen, alkyl (such as lower alkyl, e.g., methyl or ethyl), hydroxyl, acyl (such as lower acyl), acyloxy (such as lower acyloxy), or alkoxy (such as lower alkoxy, e.g., methoxy); at least one of $R_6$ and $R_7$ is hydroxyl, acyl (such as lower acyl), or acyloxy (such as lower acyloxy); and at least two of $R_1$, $R_3$, $R_6$, and $R_7$ are hydroxyl, acyl (such as lower acyl), or acyloxy (such as lower acyloxy).

In other examples, $R_1$, $R_3$, $R_6$, and $R_7$ are independently hydrogen, alkyl (such as lower alkyl, e.g., methyl or ethyl), hydroxyl, acyl (such as lower acyl), acyloxy (such as lower acyloxy), or alkoxy (such as lower alkoxy, e.g., methoxy); at least one of $R_6$ and $R_7$ is hydroxyl or acyl (such as lower acyl); at least two of $R_1$, $R_3$, $R_6$, and $R_7$ are hydroxyl or acyl (such as lower acyl).

In other embodiments, $R_1$, $R_3$, $R_6$, and $R_7$ are independently hydrogen, hydroxyl, acyl (such as lower acyl), or acyloxy (such as lower acyloxy); at least one of $R_6$ and $R_7$ is hydroxyl, acyl (such as lower acyl), or acyloxy (such as lower acyloxy); at least two of $R_1$, $R_3$, $R_6$, and $R_7$ are hydroxyl, acyl (such as lower acyl), or acyloxy (such as lower acyloxy).

$R_1$, $R_3$, $R_6$, and $R_7$ may also independently be hydrogen, hydroxyl acyl (such as lower acyl), or acyloxy (such as lower acyloxy); at least one of $R_6$ and $R_7$ is hydroxyl; at least two of $R_1$, $R_3$, $R_6$, and $R_7$ are hydroxyl.

Exemplary compounds useful in a disclosed method herein have a structure according to Formula I or II wherein $R_1$, $R_3$, $R_6$ and $R_7$ are as set forth below in Table A below, and the remaining substituents are as previously described.

TABLE A

Exemplary $R_1$, $R_3$, $R_6$, and $R_7$ substituents for Formula I or II

| Example | $R_1$ | $R_3$ | $R_6$ | $R_7$ |
|---|---|---|---|---|
| 1 | —H | —H | —OH | —H |
| 2 | —H | —H | —H | —OH |
| 3 | —H | —H | —OH | —OH |
| 4 | —OH | —H | —OH | —H |
| 5 | —OH | —H | —H | —OH |
| 6 | —OH | —H | —OH | —OH |
| 7 | —H | —OH | —OH | —OH |
| 8 | —OH | —OH | —OH | —H |
| 9 | —OH | —OH | —H | —OH |

In some embodiments, the 5-desoxy-flavone and/or 5-desoxy-flavonol employed in the methods disclosed herein has the formula:

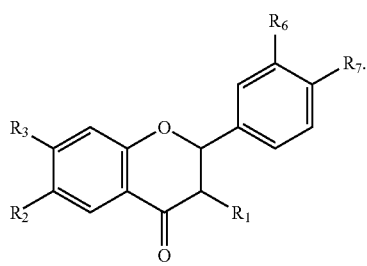

(III)

In Formula III, $R_1$, $R_2$, $R_3$, $R_6$ and $R_7$ are independently hydrogen, —$OR_{11}$, —$OC(O)R_{12}$, or unsubstituted $C_1$ to $C_5$ alkyl. $R_{11}$ and $R_{12}$ are independently hydrogen or unsubstituted $C_1$ to $C_5$ alkyl (e.g. methyl).

In some embodiments, $R_1$, $R_2$, $R_3$, $R_6$ and $R_7$ are independently hydrogen, —$OR_{11}$, —$OC(O)R_{12}$, or unsubstituted $C_1$ to $C_5$ alkyl (e.g. methyl). $R_{11}$ and $R_{12}$ may independently be hydrogen or unsubstituted $C_1$ to $C_5$ alkyl (e.g. methyl). In some embodiments, at least one of $R_1$, $R_2$, $R_3$, $R_6$ and $R_7$ is —$OR_{11}$. In certain embodiments, $R_3$ is —$OR_{11}$. $R_1$, $R_3$, $R_6$ and $R_7$ may also independently —$OR_{11}$. And in certain embodiments, $R_2$ is H.

In some embodiments, the 5-desoxy-flavone and/or 5-desoxy-flavonol employed in the methods disclosed herein has the formula:

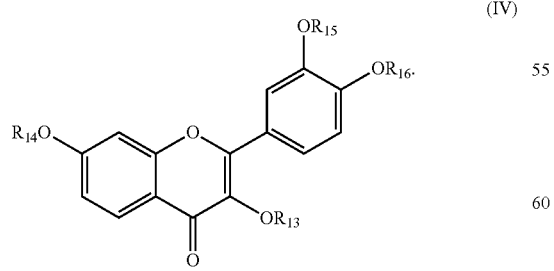

(IV)

In formula (IV), $R_{13}$, $R_{14}$, $R_{15}$ and $R_{16}$ are independently be hydrogen or unsubstituted $C_1$ to $C_5$ alkyl (e.g. methyl). In some embodiments, $R_{13}$, $R_{14}$, $R_{15}$ and $R_{16}$ are hydrogen.

A 5-desoxy-flavone (also 5(H)-flavones) useful methods disclosed herein may also include:

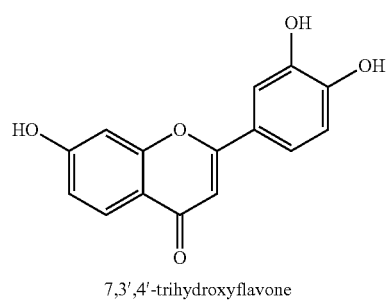

7,3′,4′-trihydroxyflavone

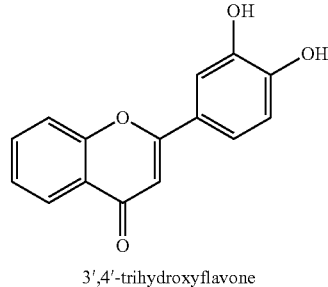

3′,4′-trihydroxyflavone

Other 5-desoxyflavonols (also 5(H)-flavonols) for use in a disclosed method include:

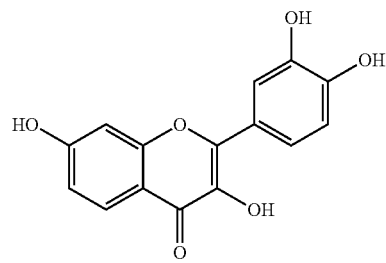 [SMILES: O=c1c(O)c(-c2ccc(O)c(O)c2)oc2cc(O)ccc12]

3,7,3′,4′-tetrahydroxyflavone
(a.k.a., fisetin)

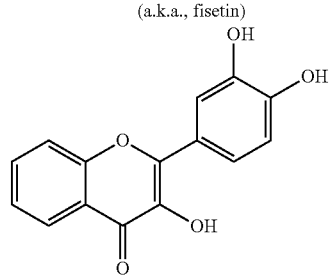

3,3′,4′-trihydroxyflavone

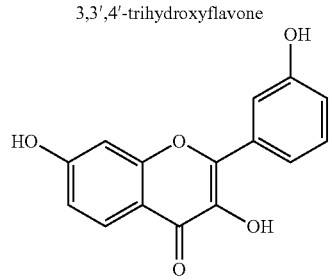

3,7,3′-trihydroxyflavone

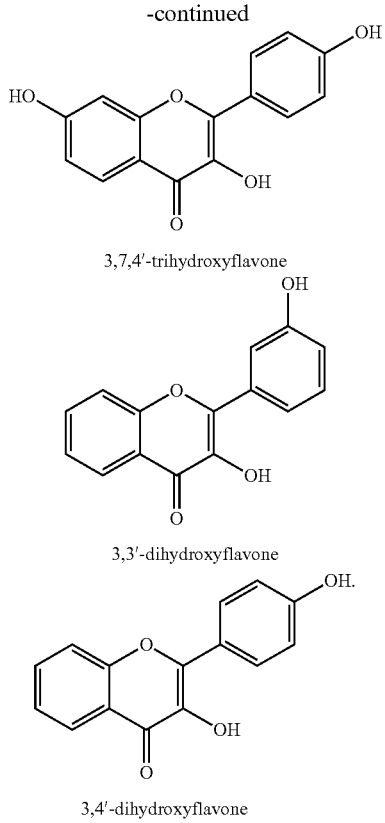

3,7,4'-trihydroxyflavone 3,3'-dihydroxyflavone 3,4'-dihydroxyflavone

In some embodiments, the methods disclosed herein employ fisetin. Fisetin is 2-(3,4-dihydroxyphenyl)-3,7-dihydroxychromen-4-one (i.e. also referred to herein as 3,7,3',4'-tetrahydroxyflavone).

In some embodiments, the 5-desoxy-flavone and/or 5-desoxy-flavonol is 3,3',4',7-tetrahydroxyflavone (fisetin), 3,3',4'-trihydroxyflavone, or 3,4',7-trihydroxyflavone. Other specific method embodiments employ 3,3',4'-trihydroxyflavone. In some methods, a compound to be administered is not 3,3',4',7-tetrahydroxyflavone (fisetin).

In certain examples, one or more flavonoids useful in disclosed methods (such as fisetin and other 5-desoxy flavonols and/or 5-desoxy flavones) can be obtained from a variety of sources. Numerous commercial suppliers of flavonoids, including 3,3',4',7-tetrahydroxyflavone (fisetin), 3,3',4'-trihydroxyflavone, 3',4',7-trihydroxyflavone, 3,3',7-trihydroxyflavone, 3,4',7-trihydroxyflavone, 3,3'-dihydroxyflavone, 3,4'-dihydroxyflavone, or 3',4'-dihydroxyflavone, are available. Such suppliers including, for example, Alexis (San Diego, Calif., USA), Aldrich (Milwaukee, Wis., USA), CalBiochem (San Diego, Calif., USA), Indofine (Hillborough, N.J., USA).

Alternatively, 5-desoxy flavonols and/or 5-desoxy flavones (such as fisetin and its derivatives as described in Examples 1-13) are naturally occurring in, and can be isolated from, various plants. For example, fisetin and other flavones are found in *Rhus* sp. (e.g., sumac), *Fragaria* sp. (e.g., strawberry), *Allium* sp. (e.g., onion), *Solanum* sp. (e.g., tomato), *Nelumbo* sp. (e.g., lotus root), *Actinidia* sp. (e.g., kiwi fruit), *Prunus* sp. (e.g., peach), *Malus* sp (e.g., apple), *Cucumis* sp. (e.g., cucumber), *Diospyros* sp. (e.g., persimmunon) *Vitis* sp. (e.g., grape) (Chas et al., Am. J. Botany, 5(3):112-9, 1918; Arai et al., J. Nutr. 139:2243-50 2000).

Such plant-derived compositions can include extracts of plants or parts thereof which, optionally, can be processed physically and/or chemically during production of the composition to extract flavonoids from the plant and so increase and enrich the flavonoid content of the isolated composition. In some examples, plant materials containing flavonoids useful in a disclosed method can be isolated by fractionation. Fractionation methods are well known in the art and described, for example, in U.S. Pat. Nos. 4,428,876 and 5,702,752. Other widely known extraction processes, which can be used alone or in combination to isolated useful flavonoids from source material (such as, plants), include differential solubility, distillation, solvent extraction, adsorptive means, differential molecular filtration, precipitation, acetone extraction, silica gel adsorption chromatography (elution with 90:10 chloroform:methanol), and HPLC (see, e.g., Son et al., Toxicol. Lett., 155:115-125, 2005).

The 5-desoxy flavonols and/or 5-desoxy flavones described above can be modified to produce derivatives, such as prodrugs. Methods for modifying such compounds are known to those of ordinary skill in the art of medicinal chemistry and include, for example, using acylating agents, such as an activated acid, for example an acid anhydride, halide or N-hydroxysuccinate to prepare an O-cyl flavone derivative. Similarly, one or more hydroxyl groups can be derivatized with alkoxy carbonyl groups to provide prodrug derivatives of flavone compounds. In certain, embodiments selective functionalization of a particular hydroxyl group to prepare a prodrug involves using a protected intermediate. Examples of suitable protecting group strategies and techniques for their implementation are known to those of ordinary skill in the art (see, Greene and Wuts, Protective Groups in Organic Synthesis, 3rd ed., New York: John Wiley & Sons, 1999).

III. Pharmaceutical Compositions

In another aspect, the present invention provides a pharmaceutical composition for use in the methods disclosed herein, wherein the pharmaceutical composition includes a pharmaceutically acceptable excipient and a 5-desoxy-flavone and/or 5-desoxy-flavonol provided herein, such as Formulae (I) to (IV) and embodiments thereof. In some embodiments, the pharmaceutical composition includes a therapeutically effective amount of the compound.

As described above, pharmaceutical compositions are provided that include the 5-desoxy-flavones and/or 5-desoxy-flavonol compound and pharmaceutically acceptable excipient, for example, in admixture with a pharmaceutically acceptable excipient. One of skill in the art will recognize that the pharmaceutical compositions may include the pharmaceutically acceptable salts of the compounds described herein.

In therapeutic and/or diagnostic applications, the compounds of the invention can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds disclosed herein are effective over a wide dosage range. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g. patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the composition. Alternatively, these agents may be part of a single dosage form, mixed together with the compound in a single composition.

Dosage forms (compositions) suitable for internal administration contain from about 1.0 milligram to about 5000 milligrams of active ingredient per unit. In these pharmaceutical compositions, the active ingredient may be present in an amount of about 0.5 to about 95% by weight based on the total weight of the composition. Another convention for denoting the dosage faun is in mg per meter squared ($mg/m^2$) of body surface area (BSA). Typically, an adult will have approximately 1.75 $m^2$ of BSA. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one tablet or capsule will provide a dose of 25 mg per kg for that patient. It will provide a dose of only 12.5 mg/kg for a 80 kg patient.

By way of general guidance, for humans a dosage of as little as about 1 milligrams (mg) per kilogram (kg) of body weight and up to about 10000 mg per kg of body weight is suitable as a therapeutically effective dose. Preferably, from about 5 mg/kg to about 2500 mg/kg of body weight is used. Other preferred doses range between 25 mg/kg to about 1000 mg/kg of body weight. However, a dosage of between about 2 milligrams (mg) per kilogram (kg) of body weight to about 400 mg per kg of body weight is also suitable for treating some cancers.

Intravenously, the most preferred rates of administration can range from about 1 to about 1000 mg/kg/minute during a constant rate infusion. A pharmaceutical composition of the present invention can be administered in a single daily dose, or the total daily dosage may be administered in divided doses of two, three, or four times daily. The composition is generally given in one or more doses on a daily basis or from one to three times a week.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. For example, the compounds described above are equally applicable to the methods and pharmaceutical compositions described herein. References cited throughout this application are incorporated by reference herein in their entirety for all purposes, whether previously specifically incorporated or not.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

A. RESEARCH DESIGN AND METHODS

1. Mice

C57BL/6-Ins2$^{Akita}$ (Akita) mice in the C57BL/6 background and C57BL/6 control mice were purchased from The Jackson Laboratories (Bar Harbor, Me.). Ins2$^{Akita}$ is a model of type 1 diabetes [10]. The Akita spontaneous mutation is an autosomal dominant mutation in the insulin II gene. This missense mutation results in an amino acid substitution which corresponds to the seventh amino acid position of the insulin II A chain. The mice were maintained an a 12-h light/dark cycle and fed a high fat mouse chow (30E, Harlan) without or with fisetin supplementation (0.05%) ad libitum beginning at 6 weeks of age until they were killed at 24 weeks (5½ months). The animal studies and the protocols were approved by the Salk Institute IACUC.

Blood was taken for determination of glucose and hemoglobin glycation at 3 months and then just before sacrifice. Spot urine samples were obtained 1 week before sacrifice. Nerve conduction velocity and thermal hypoalgesia were measured just before sacrifice.

2. Measurement of Urine Albumin and Creatinine

Urine albumin concentration was determined by competitive enzyme-linked immunoadsorbent assay using an Albuwell M kit (Exocell, Philadelphia, Pa.). Urine creatinine concentration was determined by Jaffe's reaction of alkaline picrate with creatinine using a Creatinine Companion kit (Exocell). Results are expressed as the urine albumin-to-creatinine ratio (micrograms per milligram).

3. Kidney Protein Analysis

Kidneys were homogenized in phosphate buffered saline containing protease and phosphatase inhibitors. Equal amounts of protein, as determined by the BCA assay (Pierce), were solubilized in SDS-sample buffer containing 0.1 mM $Na_3VO_4$ and 1 mM phenylmethylsulfonyl fluoride (PMSF), boiled for 5 min and either analyzed immediately or stored frozen at −70° C. Proteins were separated on 10% SDS-polyacrylamide gels and transferred to nitrocellulose. Equal loading and transfer of the samples was confirmed by staining the nitrocellulose with Ponceau-S. Transfers were blocked for 1 h at room temperature with 5% nonfat milk in TBS/0.1% Tween 20 and then incubated overnight at 4° C. in the primary antibody diluted in 5% BSA in TBS/0.05% Tween 20. The primary antibodies used were: rabbit anti-osteopontin (Millipore) and actin-HRP (Cell Signaling). The transfers were rinsed with TBS/0.05% Tween 20 and incubated for 1 h at room temperature in horseradish peroxidase-goat anti-rabbit or goat anti-mouse (Biorad, Hercules, Calif.) diluted ⅕₀₀₀ in 5% nonfat milk in TBS/0.1% Tween 20. The immunoblots were developed with the Super Signal reagent (Pierce, Rockford, Ill.).

4. Motor Nerve Conduction Studies

Conduction velocity of large myelinated motor fibers in the sciatic:tibial nerve system was measured in mice under isoflurane anesthesia with nerve temperature maintained at 37° C., as previously described (Calcutt et al. Diabetes 39:663-666, 1990). Briefly, stimulating electrodes were placed at the left sciatic notch and Achilles tendon and recording electrodes placed in the interosseus muscles of the ipsilateral hind paw. Electromyograms were recorded on a storage oscilloscope after stimulation at each site using single square waves (5 v, 0.05 ms) and motor nerve conduction velocity (MNCV) calculated using the peak to peak distance of the resulting M waves and the distance between the two stimulation sites. The median of 3 separate MNCV measurements was used to represent values for each mouse.

5. Thermal Latency Response

Mice were placed in an observation chamber on the surface (floor temperature 30° C.) of a modified Hargreaves apparatus (UARD, San Diego, Calif.) and allowed to acclimate for 5 min. For measurement of thermal response latency, a heat source that warmed the chamber surface at approximately 1° C./sec was moved underneath the hind paw and the time to foot withdrawal recorded automatically. The procedure was repeated 4 times on the same paw at 5 min intervals and the median of values 2-4 used to represent the thermal response latency.

6. Measurement of C-Reactive Protein

C-reactive protein in serum was measured by SDS-PAGE and Western blotting analysis of mouse serum using an antibody from R&D.

7. Open Field Test

The open field test was performed using MED Associates hardware and the Activity Monitor software according to the manufacturer's instructions (MED Associates Inc, St. Albans, Vt., USA). The open-field activity monitoring system contains a subject containment environment (chamber), infrared (I/R) sources and sensors. To perform the test, each mouse was placed in the testing chamber and the activity tracked by the Activity Monitor software for 30 min. The scanning was done every 50 ms. The behavioral parameters derived from the open field test included the following: distance traveled, ambulatory time and counts, stereotypic counts and time, resting time, vertical counts and time, jumping counts and time, average velocity, and ambulatory episodes.

8. Oxidative Glutamate Toxicity

Cell viability was determined by a modified version of 3-(4,5-dimethylthiazol-2-yl)-2,5-diphenyl tetrazolium bromide (MTT) assay based on the standard procedure (Hansen M B et al. J. Immunol. Methods 119:203-210, 1989). Briefly, cells were seeded onto 96-well microtiter plates at a density of $5\times10^3$ cells per well. The next day, the medium was replaced with DMEM supplemented with 7.5% DFCS and the cells were treated with the different fisetin derivatives alone or in the presence of 5 mM glutamate. Twenty four hours later, the medium in each well was aspirated and replaced with fresh medium containing 2.5 μg/ml MTT. After 4 hours of incubation at 37° C., cells were solubilized with 100 μA of a solution containing 50% dimethylformamide and 20% SDS (pH 4.7). The absorbance at 570 nm was measured on the following day with a microplate reader (Molecular Devices). Results obtained from the MTT assay correlated directly with the extent of cell death as confirmed visually. Controls employing wells without cells were used to determine the effects of the agents upon the assay chemistry. Results are shown in Table 2.

9. In Vitro Ischemia

Briefly, cells were seeded onto 96-well microtiter plates at a density of $5\times10^3$ cells per well. The next day, the medium was replaced with DMEM supplemented with 7.5% DFCS and the cells were treated with 20 μM iodoacetic acid (IAA) alone or in the presence of the different fisetin derivatives. After 2 h the medium in each well was aspirated and replaced with fresh medium without IAA but containing the fisetin derivatives. 20 h later, the medium in each well was aspirated and replaced with fresh medium containing 2.5 μg/ml MTT. After 4 h of incubation at 37° C., cells were solubilized with 100 μl of a solution containing 50% dimethylformamide and 20% SDS (pH 4.7). The absorbance at 570 nm was measured on the following day with a microplate reader (Molecular Devices). Results obtained from the MTT assay correlated directly with the extent of cell death as confirmed visually. Controls included compound alone to test for toxicity and compound with no cells to test for interference with the assay chemistry. Results are shown in Table 2.

TABLE 2

| Compound | EC50 oxid. glut. tox. (μM) | EC50 in vitro ischemia (μM) |
|---|---|---|
| 3,7,3',4'-tetrahydroxyflavone (fisetin) | <10 | >1 |
| 7,6-dimethoxy-3'-4'-diethoxy-3-hydroxyflavone | <10 | >1 |
| 7,6-dimethoxy-3'-4'-diethoxyflavone | — | ND |
| 7,6-dimethoxy-3'-methoxyflavone | — | ND |
| 7,6-dimethyl-3'-4'-diethoxyflavone | — | >1 |

TABLE 2-continued

| Compound | EC50 oxid. glut. tox. (μM) | EC50 in vitro ischemia (μM) |
|---|---|---|
| 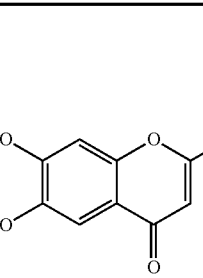 | <10 | <1 |
| 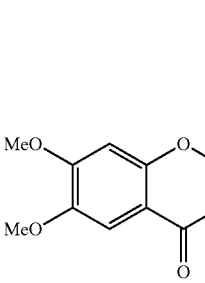 | <10 | 1 |
| 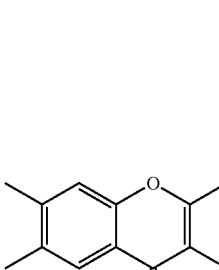 | <10 | <1 |
| 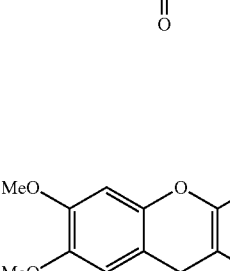 | <10 | >1 |
| 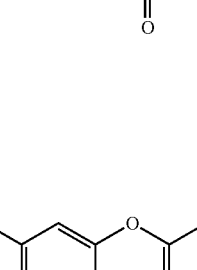 | <10 | <1 |
| (structure) | <10 | <1 |
| (structure) | >10 | >1 |
| (structure) | <10 | >1 |

10. Specificity of Antisera and Inhibition of Glycation by Fisetin

In reference to FIG. 1, BSA was incubated with either 100 mM glucose (G) or 100 mM methylglyoxal (MG) for 14 days at 37° C. plus or minus 100 μM fisetin. The BSA was dialyzed vs. PBS run on SDS-PAGE and blotted with anti-carboxymethyl lysine (CML) (a glucose AGE) or anti-MG adducts from Dr. Brownlee. In FIG. 1, panel A, Anti-CML shows reaction with glucose glycated BSA. In FIG. 1, panel B, anti-MG only reacts with MG treated BSA and also causes protein polymerization. In FIG. 1, panel C, co-incubation with fisetin results in inhibition of glucose glycation in 2 assays, Western blotting with a-CML (BL, hatched bars) and a fluorescence assay for protein glycation (FL, clear bars). In FIG. 1, panel D, fisetin inhibited protein glycation caused by high glucose exposure of human brain microvascular cells. Cells were exposed to either 5 mM (−Glu) or 25 mM (+Glu) glucose for 5 days plus (F) or minus (C) 1 μM fisetin. Cells were then harvested and blotted with either anti-CML or MG antisera. The data show that high glucose increased both CML and MG adducts and that this increase is blocked, at least in part, by fisetin. Importantly, fisetin also inhibits the endogenous glycation of some proteins in low glucose medium.

11. The Relationship Between Mg Metabolism and Nerve Cell Death

Figure 2:
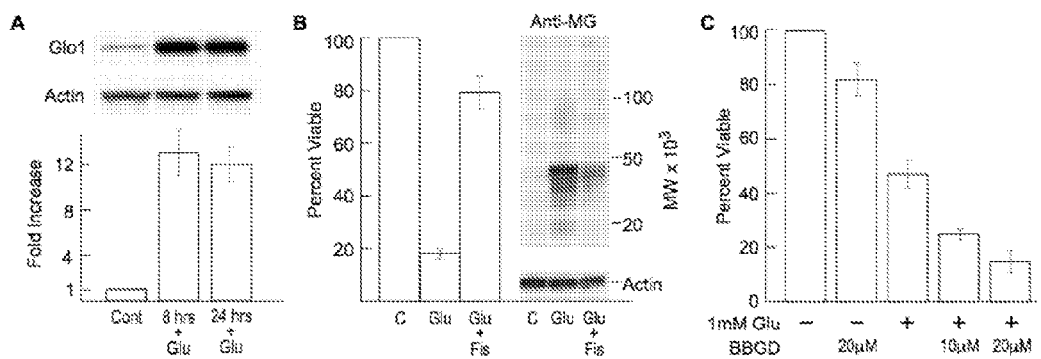
FIG. 2 illustrates the relationship between methylglyoxal metabolism and nerve cell death.

Panel (A) of FIG. 2 shows the pre-conditioning concentrations of glutamate up-regulate glyoxylase-1 (Glo-1) expression. HT-22 nerve cells were exposed to 0.5 mM glutamate and Glo-1 expression monitored at 8 and 24 hrs. In panel (B) of FIG. 2, Fisetin is shown to prevent both cell death and protein glycation. HT-22 cells were exposed to 5 mM glutamate in the presence or absence of 2 µM fisetin. MG adducts were determined by Western blotting 8 hrs after glutamate exposure and viability after 24 hrs. Actin is at the bottom of the blot. In panel (C) of FIG. 2, the Glo-1 inhibitor s-p-bromobenzylglutathione (BGD) is shown to potentiate cell death. HT-22 cells were exposed to 1 mM glutamate plus or minus 10 or 20 µM BBGD. While in the absence of glutamate 20 µM BBGD is only mildly toxic, in the presence of glutamate it greatly potentiates cell death.

12. Fisetin Upregulation of GSH and Reduction in Glutamate Toxicity

Figure 3:
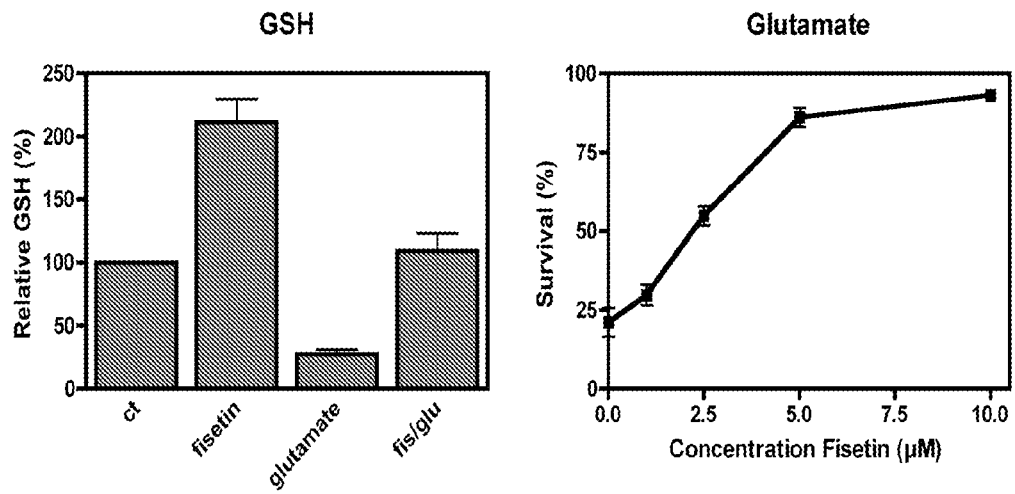
FIG. 3 illustrates fisetin upregulation of GSH and reduction in glutamate toxicity.

As shown in panel (A) of FIG. 3, HT22 cells were untreated (ct) or treated with 10 µM fisetin (fis) in the absence of presence of 5 mM glutamate for 24 hr and GSH was measured enzymatically and normalized to protein. As shown in panel (B) of FIG. 3, HT22 cells in 96-well plates were treated with 5 mM glutamate and the indicated concentrations of fisetin. MTT reduction was measured after 24 hr.

13. Fisetin Improvement of Indices of Nerve Function in STZ-Diabetic Rats

Figure 4:
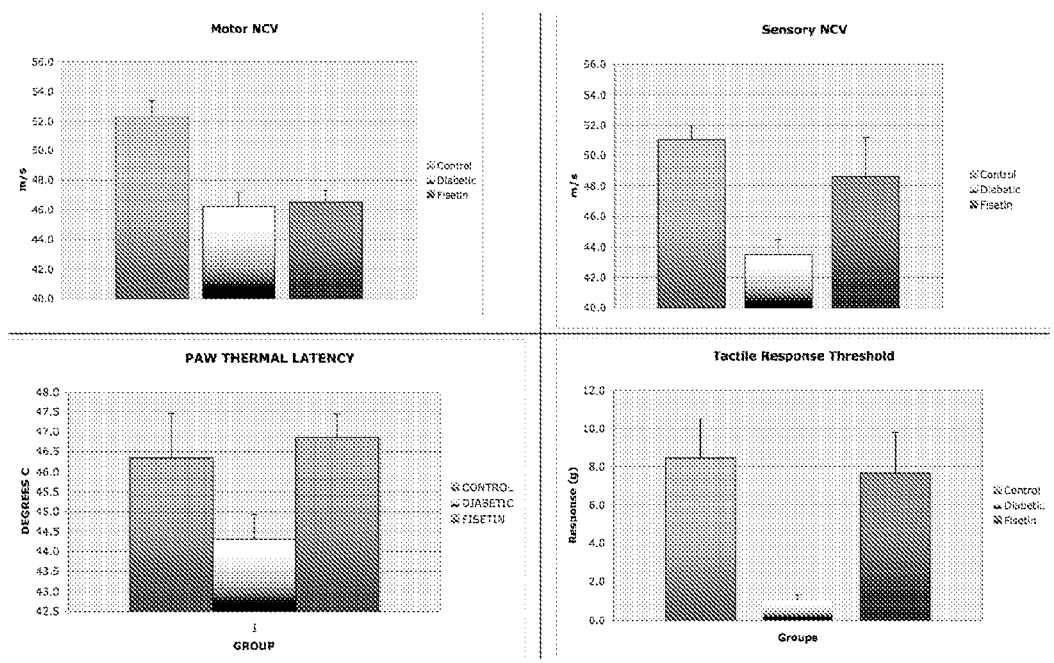
FIG. 4 illustrated fisetin improvement of indices of nerve function in STZ-diabetic rats.

Adult female Sprague-Dawley rats were made diabetic with STZ and treated with vehicle or 25 mg/kg/day fisetin for 8 weeks. Large fiber function was tested by measuring nerve conduction velocity and paw withdrawal to touch and small fiber function by paw withdrawal to noxious heat. Diabetes-induced SNCV slowing, tactile allodynia and thermal hyperalgesia were ameliorated by fisetin treatment, which did not alter the severity of diabetes (data not shown). Results are shown in FIG. 4. Data are mean±SEM of N=4-8/group.

Figure 5:
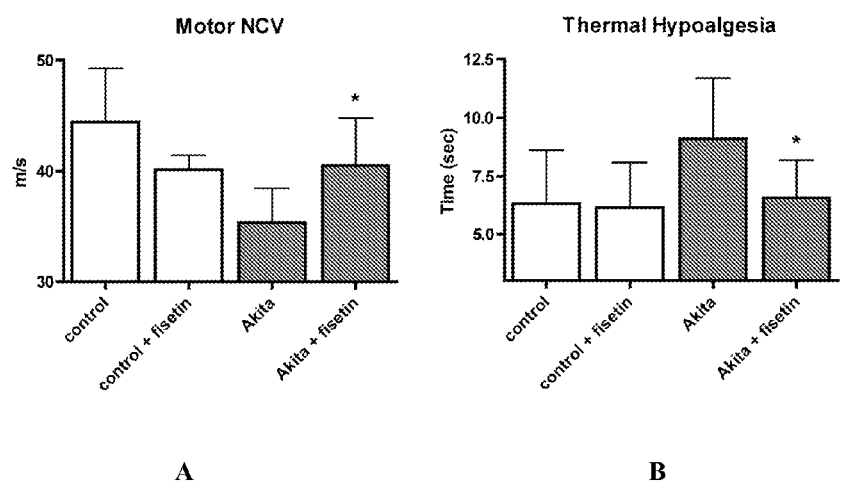
FIG. 5: illustrates fisetin reduction of the peripheral nerve complications of diabetes in Akita mice.

14. Fisetin Reduces the Peripheral Nerve Complications of Diabetes in Akita Mice Male Akita mice were fed control diet or fisetin (0.05%) for 18 weeks beginning at 6 weeks of age. Large fiber function was tested by measuring motor nerve conduction velocity and small fiber function by paw withdrawal to noxious heat. Diabetes-induced MNCV slowing and thermal hypoalgesia were ameliorated by fisetin treatment. All data are mean±SD of N=5-7/group. In FIG. 5, * indicates significantly different from Akita alone as determined by ANOVA followed by Tukey post test. P<0.05. See FIG. 5.

15. Fisetin Reduces the Kidney Complications of Diabetes in Akita Mice

Figure 6:
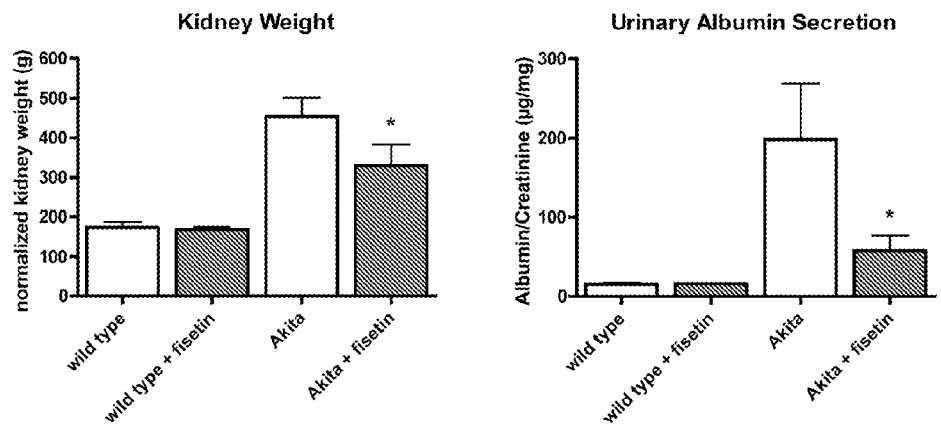
FIG. 6 illustrates fisetin reduction of kidney complications of diabetes in Akita mice.

Male Akita mice were fed control diet or fisetin (0.05%) for 18 weeks beginning at 6 weeks of age. Kidney hypertrophy was assessed by weighing the kidneys. See FIG. 6 (A). Kidney function was assessed by measuring the albumin/creatinine ratio in the urine. See FIG. 6 (B). Fisetin reduced diabetes-induced renal hypertrophy and proteinuria. All data are mean±SD of N=5-7/group. In FIG. 6, * indicates significantly different from Akita alone as determined by ANOVA followed by Tukey post test. weight P<0.01, albumin P<0.001.

16. Fisetin Reduces Anxiety in Akita Mice

Figure 7:
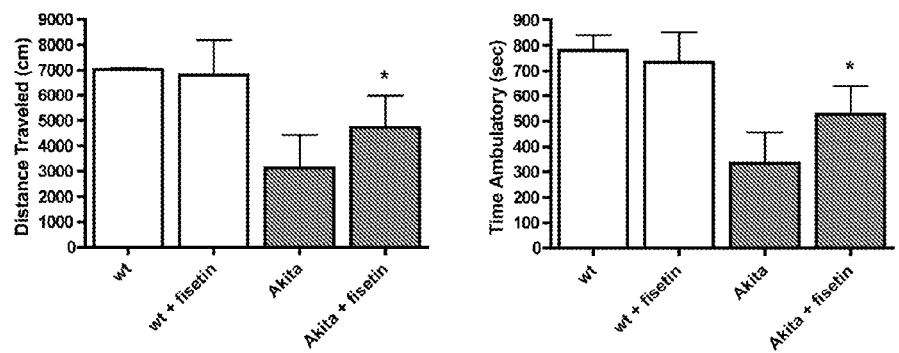
FIG. 7 illustrates fisetin reduction of anxiety in Akita mice.

Male Akita mice were fed control diet or fisetin (0.05%) for 18 weeks beginning at 6 weeks of age. Locomotor activity was measured in the open field test. Decreased locomotor activity is an indicator of elevated anxiety which is characteristic of diabetics in poor glycemic control. Fisetin restored locomotor activity to nearly control levels. All data are mean±SD of N=5-7/group. In FIG. 7, * indicates significantly different from Akita alone as determined by ANOVA followed by Tukey post test. distance P<0.05; time P<0.02

17. Fisetin Improves Kidney Function in STZ-Diabetic Rats

Figure 8:
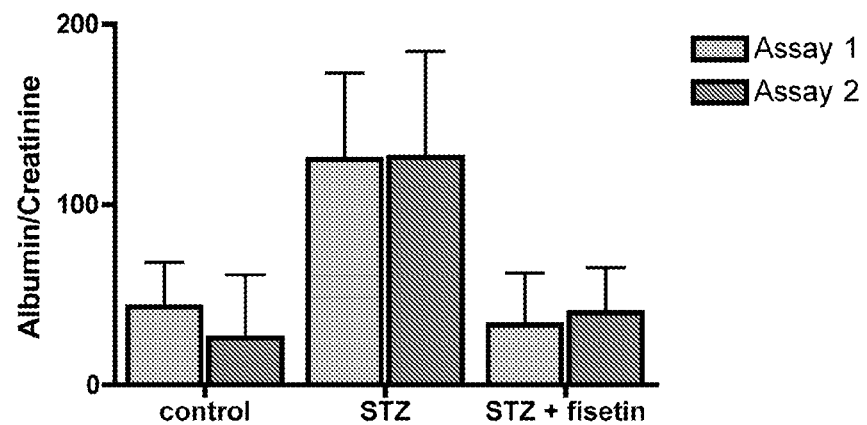
FIG. 8 illustrates that fisetin improves kidney function in STZ-diabetic rats.

Adult female Sprague-Dawley rats were made diabetic with STZ and treated with vehicle or 25 mg/kg/day fisetin. Kidney function was assessed by measuring the albumin/creatinine ratio in the urine at 6 and 8 weeks following induction of diabetes. Fisetin reduced diabetes-induced proteinuria. Data are mean±SEM of N=7-8/group. See FIG. 8.

18. Fisetin Inhibits Diabetes-Induced Increases in Serum C-Reactive Protein

C-reactive protein is an acute phase protein that increases during chronic inflammation such as is seen in diabetes. Equal amounts of serum from wild type, wild type+fisetin, Akita and Akita+fisetin mice were analyzed by SDS-PAGE and immunoblotting with an antibody to C-reactive protein. Samples from 6-7 mice were analyzed and the average intensity of the C-reactive protein band determined. The data were analyzed by ANOVA followed by Tukey's post test. * P<0.001. See FIG. 9**.

Figure 10:
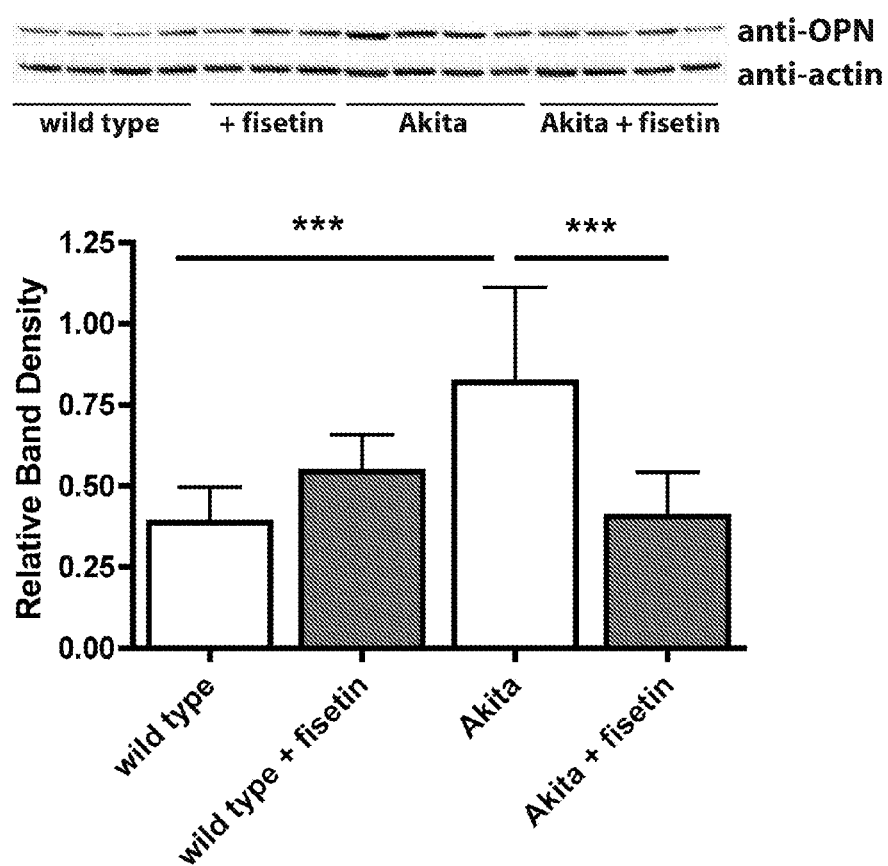
FIG. 10 illustrates that diabetes-dependent upregulation of osteopontin (OPN) is prevented by fisetin.

19. Diabetes-Dependent Upregulation of Osteopontin (OPN) is Prevented by Fisetin OPN is a key regulator of the pathophysiological changes associated with diabetic nephropathy (Nicolas et al. Kidney Int. advance online publication, 3 Feb. 2010). As shown in FIG. 10, kidneys from wild type, wild type+fisetin, Akita and Akita+fisetin mice were homogenized in PBS containing phosphatase and protease inhibitors and equal amounts of protein were analyzed by SDS-PAGE and immunoblotting with an antibody to OPN and actin as a loading control. Kidney samples from 6-7 mice were analyzed and the average intensity of the OPN band normalized to actin is shown in the graph. Representative blots are shown above. In FIG. 10, the data was analyzed by ANOVA followed by Tukey's post test. *** P<0.001

B. RESULTS

1. Metabolic Parameters

Male Akita mice develop hyperglycemia by 4 weeks of age [11]. We tested blood glucose in all animals at 12 weeks and again just before sacrificing the animals at 24 weeks. At this time, blood glucose and GHb were significantly elevated in the Akita mice (Table 1). These changes were not affected by the presence of fisetin in the diet. The Akita mice also showed significant weight loss relative to their wild type counterparts and this was also not altered by fisetin in the diet. Fisetin had no effect on the same metabolic parameters in the wild type mice. Although fisetin had no effect on the development and maintenance of hyperglycemia in the Akita mice, we tested its effects on the development of several of the major complications of hyperglycemia including diabetic nephropathy and diabetic neuropathy.

TABLE 1

Metabolic Parameters of Akita Mice

| Phenotype | Weight | Blood Glucose | HbA1c |
| --- | --- | --- | --- |
| Wild type | 29.5 ± 2.2 | 52.2 ± 32 | 4.9 ± 0.2 |
| Wild type + fisetin | 32.8 ± 3.1 | 73.0 ± 29 | 5.2 ± 0.4 |
| Akita | 23.9 ± 1.7* | 591.4 ± 78* | 17.7 ± 3.5* |
| Akita + fisetin | 23.0 ± 2.3* | 560.1 ± 86* | 16.0 ± 1.6* |

2. Kidney Hypertrophy and Proteinuria

Upon sacrifice, the kidneys were weighed and those from the Akita mice were much larger than the kidneys from wild type mice, consistent with the hypertrophy associated with diabetic neuropathy in this strain of mice [12]. The diabetes-induced increase in kidney size was greatly reduced by fisetin (FIG. 6). Fisetin had no effect on kidney weight in wild type mice. In agreement with the increase in kidney weight, spot urine tests revealed significant proteinuria in the Akita mice (FIG. 6) that was almost completely prevented by the presence of fisetin in the diet. Fisetin had no effect on the albumin/creatinine ratio in wild type mice.

3. Sensory Measures

As a measurement of the development of sensory deficits indicative of diabetic neuropathy we tested the sensitivity of the hind paw to heat. As reported previously [13], Akita mice showed a modest but statistically significant increase in hind paw thermal latency (FIG. 5B) indicating the presence of sensory hypoalgesia. The development of sensory hypoalgesia in the hind paw was prevented by the presence of fisetin in the diet. Fisetin had no effect on hind paw thermal latency in the wild type mice.

4. Nerve Conduction Studies and Intradermal Nerve Fiber Density

Nerve conduction velocity was measured in the motor neurons of the mice. The Akita mice showed a significant decrease in motor nerve conduction velocity (FIG. 5A) and this was prevented by the presence of fisetin in the diet. Fisetin had no effect on motor nerve conduction velocity in the wild type mice. Despite the changes in hind paw thermal latency and motor nerve conduction velocity, the Akita mice did not show clear changes in intraepidermal nerve fiber density (not shown).

5. Open Field Test

Akita mice were reported to display significantly decreased locomotor activity in the open field test coupled with a significantly increased time of immobilization [14]. These results were interpreted as indicative of anxiety behavior, an additional complication of many patients with diabetes [15]. As shown in FIG. 7, we confirmed these results with the Akita mice. In contrast, Akita mice fed fisetin showed a significant reduction in these anxiety-related symptoms with both the distance traveled and ambulatory episodes in the open field test restored to near normal values. Fisetin had no effect on the behavior of the wild type mice in the open field test.

6. Inflammatory Markers

Figure 9:
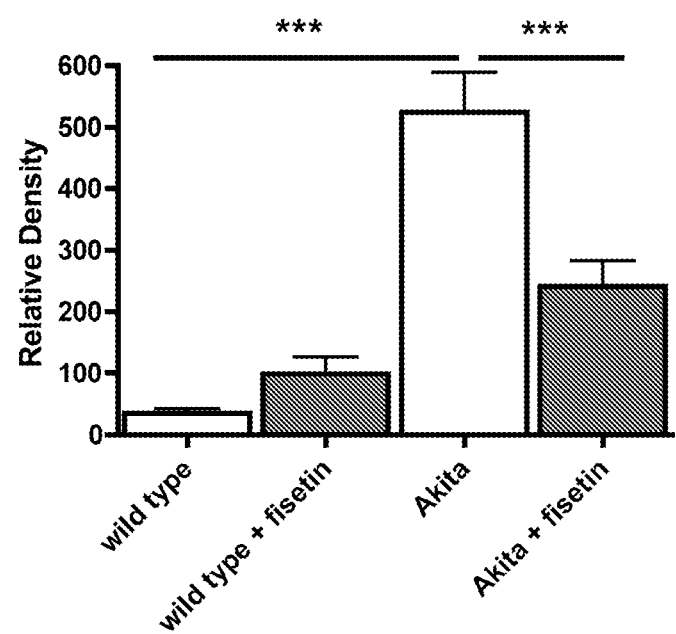
FIG. 9 illustrates fisetin inhibition of diabetes-induced increases in serum C-reactive protein.

Inflammation is developing as a major contributor to many diseases, including the complications of diabetes [16]. Fisetin is reported to have anti-inflammatory activity against both peripheral [17] and CNS [8] immune cells. To determine if the anti-inflammatory activity of fisetin could play a role in the prevention of diabetic complications in the Akita mice, we examined the levels of C-reactive protein, a marker of chronic systemic inflammation associated with diabetes, in the serum. As shown in FIG. 9, C-reactive protein was significantly increased in the serum of Akita mice and this increase was largely prevented by the fisetin-rich diet.

C. REFERENCES

[1] Stirban A, Rosen P, Tschoepe D (2008) Complications of Type 1 diabetes: New molecular findings. Mt Sinai J Med 75: 328-351; [2] Calcutt N A, Cooper M E, Kern T S, Schmidt A M (2009) Therapies for hyperglycemia-induced diabetic complications: from animal models to clinical trials. Nature Rev Drug Discov 8: 417-429; [3] Maher P (2009) Modulation of multiple pathways involved in the maintenance of neuronal function during aging by fisetin. Genes Nutr Sep 10 [Epub ahead of print]; [4] Yuan H, Lanting L, Xu Z-G, et al. (2008) Effects of cholesterol-tagged small interfering RNAs targeting 12/15-lipoxygenase on parameters of diabetic nephropathy in a mouse model of type 1 diabetes. Am J Physiol Renal Physiol 295: F605-F617; [5] Li Y, Maher P, Schubert D (1997) A role of 12-lipoxygenase in nerve cell death caused by glutathione depletion. Neuron 19: 453-463; [6] Seiler A, Schneider M, Forster H, et al. (2008) Glutathione peroxidase 4 senses and translates oxidative stress into 12/15-lipoxygenase dependent- and AIF-mediated cell death. Cell Metabolism 8: 237-248; [7] Maher P, Akaishi T, Abe K (2006) Flavonoid fisetin promotes ERK-dependent long-term potentiation and enhances memory. Proc Natl Acad Sci USA 103: 16568-16573; [8] Zheng L T, Ock J, Kwon B-M, Suk (2008) Suppressive effects of flavonoid fisetin on lipopolysaccharide-induced microglial activation and neurotoxicity. Int Immunopharmacol 8: 484-494; [9] Geraets L, Haegens A, Brauers K, et al. (2009) Inhibition of LPS-induced pulmonary inflammation by specific flavonoids. Biochem Biophys Res Commun 382: 598-603; [10] Yoshioka M, Kayo T, Ikeda T, Koizumi A (1997) A novel locus, Mody4, distal to D7Mit189 on chromosome 7 determines early-onset NIDDM in nonobese C57BL/6 (Akita) mutant mice. Diabetes 46: 887-894; [11] Barber A J, Antonetti D A, Kern T S, et al. (2005) The Ins2Akita mouse as a model of early retinal complications in diabetes. Invest Ophthalmol V is Sci 46: 2210-2218; [12] Gurley S B, Clare S E, Snow K P, Hu A, Meyer T W, Coffman T M (2006) Impact of genetic background on nephropathy in diabetic mice. Am J Physiol Renal Physiol 290: F214-F222; [13] Sullivan K A, Hayes J M, Wiggin T D, et al. (2007) Mouse models of diabetic neuropathy. Neurobiol Dis 28: 276-285; [14] Asakawa A, Toyoshima M, Inoue K, Koizumi A (2007) Ins2Akita mice exhibit hyperphagia and anxiety behavior via the melanocortin system. Int J Mol Med 19: 649-652; [15] Reagan L P, Grillo C A, Piroli G G (2008) The As and Ds of stress: Metabolic, morphological and behavioral consequences. Eur J Pharmacol 585: 64-75; [16] King GL (2008) The role of inflammatory cytokines in diabetes and its complications. J Periodontol 79: 1527-1534; [17] Wang L, Tu Y-C, Lian T-W, Hung J-T, Yen J-H, Wu M-J (2006) Distinctive antioxidant and antiinflammatory effects of flavonols. J Agric Food Chem 54: 9798-9804; [18] Brownlee M (2001) Biochemistry and molecular cell biology of diabetic complications. Nature 414: 813-820; [19] Maher P (2010) Modulation of multiple pathways involved in the maintenance of neuronal function by fisetin. In: Packer L, Sies H, Eggersdorfer M, Cadenas E (eds) Micronutrients and Brain Health. CRC Press, Boca Raton, Fla., pp 189-206; [20] Ishige K, Schubert D, Sagara Y (2001) Flavonoids protect neuronal cells from oxidative stress by three distinct mechanisms. Free Radic Biol Med 30: 433-446; [21] Sagara Y, Vahnnasy J, Maher P (2004) Induction of PC12 cell differentiation by flavonoids is dependent upon extracellular signal-regulated kinase activation. J Neurochem 90: 1144-1155; [22] Biessels G J, Deary I J, Ryan C M (2008) Cognition and diabetes: a lifespan perspective. Lancet Neurol 7: 184-190; [23] Choeiri C, Hewitt K, Durkin J, Simard C J, Renaud J-M, Messier C (2005) Longitudinal evaluation of memory performance and peripheral neuropathy in the Ins2C96Y Akita mice. Behav Brain Res 157: 31-38; [24] Hatcher H, Panalp R, Cho J, Torti F M, Torti S V (2008) Curcumin: from ancient medicine to current clinical trials. Cell Mol Life Sci 65: 1631-1652; [25] Ji H-F, Li X-J, Zhang H-Y (2009) Natural products and drug discovery. EMBO Rep 10: 194-200; [26] Sharma S, Kulkarni S K, Agrewala J N, Chopra K (2006) Curcumin attenutates thermal hyperalgesia in a diabetic mouse model of neuropathic pain. Eur J Pharmacol 536: 256-261; [27] Sharma S, Kulkarni S K, Chopra K (2006) Curcumin, the active principle of tumeric (Curcuma Tonga), ameliorates diabetic nephropathy in rats. Clin Exp Pharmacol Physiol 33: 940-945; [28] Sharma S, Anjaneyulu M, Kulkarni S K, Chopra K (2006) Resveratrol, a polyphenolic phytoalexin, attenuates diabetic nephropathy in rats. Pharmacol 76: 69-75; [29] Sharma S, Kulkarni S K, Chopra K (2007) Effect of resveratrol, polyphenolic phytoalexin, on thermal hyperalgesia in a mouse model of diabetic neuropathic pain. Fundam Clin Pharmacol 21: 89-94; [30] Anjaneyulu M, Chopra K (2004) Quercetin attenuates thermal hyperalgesia and cold allodynia in STZ-induced diabetic rats. Indian J Exp Biol 42: 766-769; [31] Anjaneyulu M, Chopra K (2004) Quercetin, an anti-oxidant bioflavonoid, attenuates diabetic nephropathy in rats. Clin Exp Pharmacol Physiol 31: 244-248; [32]Valensi P, Le Devehat C, Richard J-L, et al. (2005) A mulitcenter, double-blind, safety study of QR-333 for the treatment of symptomatic diabetic peripheral neuropathy A preliminary report. J Diabetes Compl 19: 247-253; [33] Manach C, Williamson G, Morand C, Scalbert A, Remesy C (2005) Bioavailability and bioefficacy of polyphenols in humans. I. Review of 97 bioavailability studies. Amer J Clin Nutr 81: 230S-242S; [34] Prasain J K, Barnes S (2007) Metabolism and bioavailability of flavonoids in chemoprevention: Current analytical strategies and future prospects. Mol Pharmaceut 4: 846-864; [35] Shia C-S, Tsai S-Y, Kuo S-C, Hou Y-C, Chao P-D L (2009) Metabolism and pharmacokinetics of 3,3',4',7-tetrahydroxyflavone (fisetin), 5-hydroxyflavone and 7-hydroxyflavone and antihemolysis effects of fisetin and its serum metabolites. J Agric Food Chem 57: 83-89; [36] Stevenson D E, Cooney J M, Jensen D J, et al. (2008) Comparison of enzymically glucuronidated flavonoids with flavonoid aglycones in an in vitro cellular model of oxidative stress protection. In Vitro Cell Dev Biol Anim Epub; [37] Arai Y, Watanabe S, Kimira M, Shimoi K, Mochizuki R, Kinae N (2000) Dietary intakes of flavonols, flavones and isoflavones by Japanese women and the inverse correlation between quercetin intake and plasma LDL and cholesterol concentration. J Nutri 130: 2243-2250

What is claimed is:

1. A method of treating one or more complications of a diabetes or a vascular disease in a subject in need thereof, wherein said method comprises administering to said subject a therapeutically effective amount of a compound having the formula:

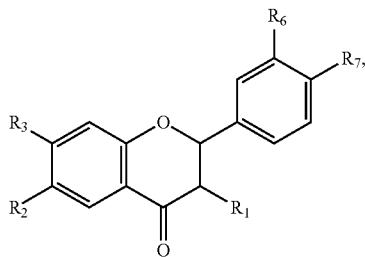

wherein, $R^1$, $R^2$, $R^3$, $R^6$ and $R^7$ are independently hydrogen, $-OR^{11}$, $-OC(O)R^{12}$, or unsubstituted $C_1$ to $C_5$ alkyl; and $R^{11}$ and $R^{12}$ are independently hydrogen or unsubstituted $C_1$ to $C_5$ alkyl.

2. The method of claim 1, wherein said complication is a nephropathy.

3. The method of claim 1, wherein said complication is a diabetic nephropathy.

4. The method of claim 1, wherein said complication is a neuropathy.

5. The method of claim 1, wherein said complication is a diabetic neuropathy.

6. The method of claim 1, wherein said complication is a retinopathy.

7. The method of claim 1, wherein said complication is a diabetic retinopathy.

8. The method of claim 1, wherein said complication is anxiety.

9. The method of claim 1, wherein said complication is a nephropathy and a neuropathy.

10. The method of claim 1, wherein said complication is an inflammation.

11. A method of decreasing C-reactive protein levels in a subject in need thereof, wherein said method comprises administering to said subject an effective amount of a compound having the formula:

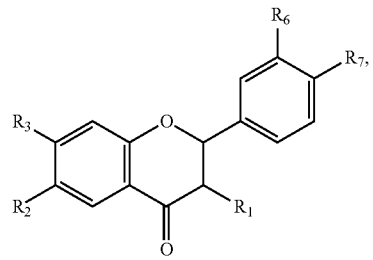

wherein, $R^1$, $R^2$, $R^3$, $R^6$ and $R^7$ are independently hydrogen, $-OR^{11}$, $-OC(O)R^{12}$, or unsubstituted $C_1$ to $C_5$ alkyl; and $R^{11}$ and $R^{12}$ are independently hydrogen or unsubstituted $C_1$ to $C_5$ alkyl.

12. The method of one of claims 1 or 11, wherein at least one of $R^1$, $R^2$, $R^3$, $R^6$ and $R^7$ is $-OR^{11}$.

13. The method of one of claims 1 or 11, wherein $R^3$ is $-OR^{11}$.

14. The method of one of claims 1 or 11, wherein $R^1$, $R^3$, $R^6$ and $R^7$ are independently $-OR^{11}$.

15. The method of one of claims 1 or 11, wherein said compound has the formula:

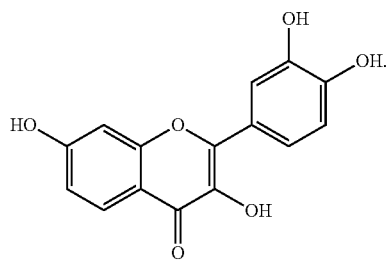 [SMILES: O=c1c(O)c(-c2ccc(O)c(O)c2)oc2cc(O)ccc12]

* * * * *

UNITED STATES PATENT AND TRADEMARK OFFICE
CERTIFICATE OF CORRECTION

| | | |
|---|---|---|
| PATENT NO. | : 8,466,195 B2 | Page 1 of 1 |
| APPLICATION NO. | : 13/255192 | |
| DATED | : June 18, 2013 | |
| INVENTOR(S) | : Maher et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 101 days.

Signed and Sealed this
Sixth Day of January, 2015

Michelle K. Lee
*Deputy Director of the United States Patent and Trademark Office*